United States Patent
Sato et al.

(12) 
(10) Patent No.: US 6,284,495 B1
(45) Date of Patent: Sep. 4, 2001

(54) METHOD FOR PRODUCING NUCLEIC ACID SUBSTANCES

(75) Inventors: Katsuaki Sato; Yoshihiro Usuda, both of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/327,681

(22) Filed: Jun. 8, 1999

(30) Foreign Application Priority Data

Jun. 12, 1998 (JP) .................................................. 10-165704

(51) Int. Cl.$^7$ ........................................................ C12P 19/30
(52) U.S. Cl. .............................................. 435/89; 435/91.1
(58) Field of Search ...................................... 435/91.1, 89

(56) References Cited

FOREIGN PATENT DOCUMENTS 3-164185    7/1991   (JP) .

OTHER PUBLICATIONS

Meng et al., *Eur. J. Biochem.*, vol. 187, (1990), pp. 373–379.*

Weng et al., *PNAS*, vol. 92, (Aug. 1995) pp. 7455–7459.*

Rebecca L. Wilson et al, Journal of Bacteriology, "Roles of the GcvA and PurR Proteins in Negative Regulation of *Escherichia coli* Glycine Cleavage Enzyme System" Aug. 1993, pp. 5129–5134.

John G. Steiert et al, Journal of Bacteriology, Regulation of the *Escherichia coli* glyA Gene by the purR Gene Product, Jul. 1990, pp. 3799–3803.

Byung Sik Shin et al, Journal of Bacteriology, "Interaction of *Bacillus subtilis* Purine Repressor with DNA" Dec., 1997, pp. 7394–7402.

* cited by examiner

*Primary Examiner*—James Ketter
(74) *Attorney, Agent, or Firm*—Oblon, Spivak, McClelland, Maier & Neustadt

(57) ABSTRACT

A nucleic acid substance is efficiently produced by cultivating a microorganism whose repressor protein for purine operon does not function in a normal manner, preferably a strain whose gene encoding the repressor protein on a chromosome (purR) is disrupted, in a culture medium so that the nucleic acid substance should accumulate in the culture medium, and collecting the substance from the culture medium.

7 Claims, 1 Drawing Sheet

US 6,284,495 B1

METHOD FOR PRODUCING NUCLEIC ACID SUBSTANCES

TECHNICAL FIELD

The present invention relates to a method for producing nucleic acid substances by fermentation. Nucleic acid substances are industrially useful as materials of seasonings and the like.

BACKGROUND ART

In the production of nucleic acid substances such as inosine, guanosine and bases thereof (hypoxanthine and guanine and the like) by fermentation, there have conventionally been used mutant strains imparted with adenine auxotropy and nucleic acid analogue resistance (Japanese Patent Publication (KOKOKU) Nos. Sho 55-2956 and Sho 55-45199) with a limited amount of adenine substances in their culture medium.

Mutant strains obtained by usual mutagenesis procedures are often introduced with mutations in their genes other than the target gene. In addition, because complicated regulation mechanisms are involved in biosynthetic pathways of nucleic acid substances, it is difficult to obtain a microorganism that produces a significant amount of nucleic acid substance. Therefore, mutant strains obtained by conventional breeding methods have not necessarily been satisfactory ones.

On the other hand, there has been disclosed a method for producing inosine or guanosine by utilizing a bacterium belonging to the genus Bacillus exhibiting enhanced purine operon expression obtained by modification of a gene sequence encoding enzymes involved in the purine biosynthesis (purine operon) (Japanese Patent Unexamined Publication (KOKAI) No. Hei 3-164185). This method is characterized in that a promoter or operator of the purine operon is modified to increase the expression level of the operon, thereby increasing the production of inosine or guanosine.

Expression of the purine operon of *Bacillus subtilis* (purEKBC(ORF)OLFMNHD where ORF represents an open reading frame of unknown function) is suppressed by an excessive amount of adenine, and also regulated by attenuation caused by guanine. Further, a repressor protein binding to the 5' flanking region of the purine operon and a gene encoding the protein (purR) have been isolated, and it has been reported that, in a *Bacillus subtilis* strain whose purR gene was disrupted, suppression by adenine as for the expression of purC-lacZ fusion gene integrated into the purine operon was reduced to about 1/10 (*Proc. Natl. Acad. Sci. USA*, 92, 7455–7549 (1995)).

In *Bacillus subtilis*, the repressor protein has been known to regulate the expression of, in addition to the genes of the purine operon, purA gene involved in the biosynthesis of adenine and genes of pyrimidine operon involved in the pyrimidine biosynthesis (1997, *J. Bacteriol.* 179, 7394–7402, H. Zalkin).

On the other hand, in *Escherichia coli*, it has been reported that the purine operon repressor also affects the expression of glyA gene involved in the biosynthesis of glycine, which is a substance of 5'-IMP (inosinic acid) biosynthesis (1990, *J. Bacteriol.* 172, 3799–3803, H. Zalkin et al.), and the expression of gcv operon genes involved in the production of $C_1$ and $CO_2$ supplied from glycine (1993, *J. Bacteriol.* 175, 5129–5134, G. V. Stauffer et al.) in addition to the genes of the purine operon.

As described above, several reports have been made about the relationship between the purine operon and inosine or guanosine production. However, there are various biosynthesis pathways involving the purR gene. Further, the purine operon of *Bacillus subtilis* encodes ten enzymes, and involved in many reactions. Thus, the biosynthesis pathways of nucleic acid substances are very complicated, and the relationship between the purR gene and accumulation of nucleic acid substances has scarcely been known.

DESCRIPTION OF THE INVENTION

The object of the present invention is to provide a method for more advantageously producing nucleic acid substances compared with conventional methods in view of the industrial importance of nucleic acid substances.

The present inventors earnestly conducted studies about the function of purR gene in order to achieve the aforementioned object, and as a result they found that *Bacillus subtilis* strain whose purR gene had been disrupted accumulated a nucleic acid substance. Thus, the present invention has been accomplished.

That is, the present invention provides:

(1) a method for producing a nucleic acid substance comprising steps of: cultivating in a culture medium a microorganism whose repressor protein for purine operon does not function in a normal manner to produce and accumulate the nucleic acid substance in the culture medium, and collecting the substance from the culture medium;

(2) the method defined in the above (1), whrerin the repressor protein does not function in a normal manner because a gene encoding the repressor protein on a chromosome of the microorganism is disrupted;

(3) the method defined in the above (1), wherein the repressor protein has the amino acid sequence shown in SEQ ID NO: 6;

(4) the method defined in the above (1), wherein the microorganism is a bacterium belonging to the genus Bacillus;

(5) The method defined in the above (4), wherein the microorganism is *Bacillus subtilis;*

(6) the method defined in the above (1), wherein the nucleic acid substance is a nucleic acid base, nucleoside or nucleotide; and (7) the method defined in the above (6), wherein the nucleic acid substance is selected from the group consisting of hypoxanthine, uracil, guanine and adenine.

For the purpose of the present invention, the expression "repressor protein for purine operon does not function in a normal manner" means that the repressor protein binds to the 5' flanking region of the purine operon, and hence the function for suppressing transcription of the operon is reduced compared with the normal level, or it is substantially eliminated.

In the present invention, the nucleic acid substance includes nucleic acid bases such as hypoxanthine, adenine, guanine, uracil, thymine and cytosine, nucleosides such as inosine, adenosine, guanosine, uridine, thymidine and cytidine, nucleotides such as inosinic acid, adenylic acid, guanylic acid, uridylic acid, thymidylic acid and cytidylic acid, and compounds composed of any one of those nucleosides or nucleotides whose ribose is replaced with deoxyribose. Among these, the nucleic acid bases are preferred. In the present invention, the nucleic acid substance includes both of purine compounds and pyrimidine compounds. Such purine compounds include purine base, and nucleosides and nucleotides having purine base. The pyrimidine compounds include pyrimidine base, and nucleosides and nucleotides having pyrimidine base. In the present invention, hypoxanthine, adenine and guanine are preferred as the purine compounds, and uracil is preferred as the pyrimidine compound

DETAILED DESCRIPTION OF THE INVENTION

Figure 1:
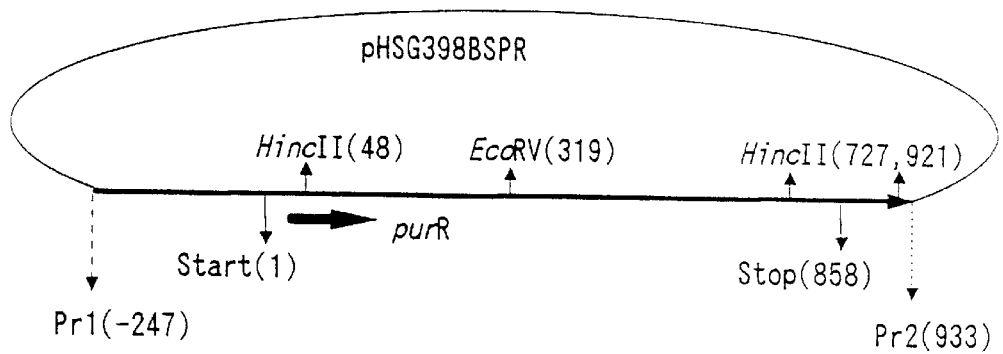
FIG. 1 represents the structure of plasmid pHSG398BSPR. The bold line indicates purR gene derived from *Bacillus subtilis* SB112. The parenthesized numbers represent positions in the coding region when the starting position is defined 1. The normal line indicates plasmid pHSG398.

The present invention will be hereinafter explained in detail.

The microorganism used for the method of the present invention is a microorganism whose repressor protein for purine operon (also referred to an merely "repressor" hereinafter) does not function in a normal manner. The microorganism is not particularly limited, so long as its genes for enzymes of biosynthesis of purine compounds form an operon, and it has a gene encoding a repressor involved in the regulation of the operon (purR). Examples of such a microorganism include bacteria belonging to the gene Bacillus and the like. Specific examples of the bacteria of the gene Bacillus include, for example, *Bacillus subtilis*, *Bacillus amyloliquefaciens* and the like.

The microorganism whose repressor does not function in a normal manner can be obtained by modifying its purR gene so that the activity of the repressor should be reduced or eliminated, or the transcription of the purR gene should be reduced or eliminated. Such a microorganism can be obtained by, for example, replacing the chromosomal purR gene with a purR gene that does not function in a normal manner (occasionally referred to as "disrupted purR gene" hereinafter) through, for example, homologous recombination based on genetic recombination techniques (Experiments in Molecular Genetics, Cold Spring Harbor Laboratory Press (1972); Matsuyama, S. and Mizushima, S., J. Bacteriol., 162, 1196 (1985)).

In the homologous recombination, when a plasmid carrying a sequence exhibiting homology with a chromosomal sequence or the like is introduced into a corresponding bacterial cell, recombination occurs at a site of the homologous sequence at a certain frequency, and thus the introduced plasmid as a whole is integrated into the chromosome. Then, by causing recombination again at the site of the homologous sequence in the chromosome, the plasmid may be removed from the chromosome. However, depending on the position at which the recombination is caused, the disrupted gene may remain on the chromosome, while the original normal gene may be removed from the chromosome together with the plasmid. By selecting such a bacterial strain, a bacterial strain in which the normal purR gene is replaced with a disrupted purR gene can be obtained.

Such a gene disruption technique based on the homologous recombination has already been established, and a method utilizing a linear DNA, method utilizing temperature sensitive plasmid or the like can be used therefore. The purR gene can also be disrupted by using a plasmid that contains the purR gene inserted with a marker gene such as drug resistance gene, and cannot replicate in a target microbial cell. That is, in a transformant that has been transformed with such a plasmid and hence acquired drug resistance, the marker gene is integrated in a chromosome DNA. It is likely that this marker gene has been integrated by homologous recombination of the purR gene present at the both sides of the marker with the purR on the chromosome, and therefore a gene-disrupted strain can efficiently be selected.

Specifically, a disrupted purR gene used for the gene disruption can be obtained by deletion of a certain region of purR gene by means of digestion with restriction enzyme(s) and the religation; by insertion of another DNA fragment (marker gene etc.) into the purR gene, by introducing substitution, deletion, insertion, addition or inversion of one or more nucleotides in a nucleotide sequence of coding region of purR gene, its promoter region or the like by means of site-specific mutagenesis (Kramer, W. and Frits, H. J., *Methods in Enzymology*, 154, 350 (1987)) or treatment with a chemical reagent such as sodium hyposulfite and hydroxylamine (Shortle, D. and Nathans, D., *Proc. Natl. Acad. Sci. U.S.A.*, 75, 270(1978)) or the like, so that the activity of the encoded repressor should be reduced or eliminated, or transcription of the purR gene should be reduced or eliminated. Among these embodiments, a method utilizing deletion of a certain region of the purR gene by digestion with a restriction exzyme and religation, or insertion of another DNA fragment into the purR gene is preferred in view of reliability and stability.

The purR gene can be obtained from a chromosomal DNA of a microorganism which has a purine operon by PCR using oligonucleotides prepared based on known nucleotide sequences of the purR gene as primers. The purR gene can also be obtained from a chromosome DNA library of a microorganism which has a purine operon by a hybridization technique using an oligonucleotide prepared based on a known nucleotide sequence of the purR gene as a probe. A nucleotide sequence of the purR gene has been reported for *Bacillus subtilis* 168 Marburg strain (GenBank accession No. D26185 (the coding region corresponds to the nucleotide numbers 118041–118898), DDBB accession No. Z99104 (the coding region corresponds to the nucleotide numbers 54439–55296). The nucleotide sequence of purR gene and the amino acid sequence coded by the gene is shown in SEQ ID NO: 5 and 6 in Sequence Listing. For the purpose of the present invention, because the purR gene is used for preparing a disrupted purR gene, it is not necessarily required to contain the full length, and it may contain a length required to cause gene disruption.

The microorganism used for obtaining the purR gene is not particularly limited, so long as its purR gene has homology of such a degree that allows homologous recombination with purR gene of a microorganism used for creation of gene-disrupted strain. However, it is normally preferable to use the same microorganism.

The primers used for PCR may be any one allowing amplification of the purR gene, and specific examples thereof include oligonucleotides having a nucleotide sequence shown in SEQ ID NO: 1 or SEQ ID NO: 2.

Examples of the marker gene include, for example, drug resistance genes such as spectinomycin resistance gene. A spectinomycin resistance gene can be obtained by preparing plasmid pDG1726 from *Escherichia coli* ECE101 strain commercially available from Bacillus Genetic Stock Center (BGSC), and excising the gene from the plasmid as a cassette.

When a drug resistance gene is used as the marker gene, a purR gene-disrupted strain can be obtained by inserting the drug resistance gene into a suitable site of the purR gene carried by a plasmid, transforming a microorganism with the plasmid, and selecting a drug resistant transformant. Disruption of purR gene on a chromosome can be confirmed by analyzing the purR gene or the marker gene on the chromosome by Southern blotting, PCR, or the like. Integration of the spectinomycin resistance gene into a chromosomal DNA can be confirmed by PCR using primers that allow amplification of the spectinomycin resistance gene (e.g., oligonucleotides having nucleotide sequences shown in SEQ ID NOS: 3 and 4).

By cultivating a microorganism whose repressor does not function in a normal manner obtained as described above in a suitable culture medium, a nucleic acid substance may be produced and accumulated in the culture medium.

As the culture medium used for the present invention, an ordinary nutrient medium containing a carbon source, nitrogen source, mineral salt, and organic trace nutrient such as amino acids and vitamins as required can be used, and the cultivation ca be performed in a conventional manner. Either a synthetic culture medium or a natural medium can be used. The carbon source and the nitrogen source used for the culture medium may be of any kinds so long as they can be utilized by a bacterial strain to be cultured.

As the carbon source, saccharides such as glucose, glycerol, fructose, sucrose, maltose, mannose, galactose, starch hydrolysates and molasses may be used, and organic acids such as acetic acid and citric acid may be used by themselves or in combination with another carbon source.

As the nitrogen source, ammonia, ammonium salts such as ammonium sulfate, ammonium carbonate, ammonium chloride, ammonium phosphate, and ammonium acetate, nitrates and the like can be used.

As the trace nutrient, amino acids, vitamins, aliphatic acids, nucleic acids, as well as peptone, casamino acid, yeast extract, soybean protein decomposition products and the like, which contain the foregoing substances, may be used. When an auxotroph mutant requiring amino acid or the like for its growth is used, it is necessary to supplement the required nutrient.

As the mineral salt, phosphates, magnesium salts, calcium salts, iron salts, manganese salts and the like may used.

The culture condition depends on the kind of microorganism to be used. For example, *Bacillus subtilis* is cultured by aeration culture while adjusting fermentation temperature to 20–50° C., and pH to 4–9. When pH decreases during cultivation, the medium may be neutralized with an alkali such as ammonia gas. A nucleic acid substance is accumulated in the culture medium by performing cultivation as described above for around 40 hours to 3 days.

After the cultivation is completed, the nucleic acid substance accumulated in the culture medium may be recovered by a known method. For example, it can be isolated by precipitation, ion exchange chromatography or the like.

If the microorganism used for the present invention is made defective for a gene encoding a nucleosidase or nucleotidase, a corresponding nucleoside or nucleotide can be accumulated. If it is imparted with adenine or guanine auxotrophy, precursors in biosynthesis pathways of these substances and related substances can be accumulated.

Further, by treating a nucleic acid base produced by the method of the present invention with purine nucleoside phosphorylase or phsophoribosyltransferase, a nucleoside or nucleotide corresponding to the base can be obtained.

BEST MODE FOR CARRYING OUT THE INVENTION

The present invention will be explained more specifically with reference to the following examples.

<1> Cloning of purR gene

A DNA fragment containing purR gene of *Bacillus subtilis* 168 Marburg strain (ATCC 6051) was obtained by PCR using chromosomal DNA of the bacterium as a template.

The chromosomal DNA was prepared as follows. The *Bacillus subtilis* ATCC 6051 strain was inoculated in 50 ml of LB medium, cultured at 37° C. overnight, then collected and lysed with a lysing solution containing 1 mg/ml of lysozyme. The lysate was treated with phenol, and then DNA was precipitated by ethanol precipitation in a usual manner. The resulting precipitates of DNA were collected by winding them on a glass rod, washed, and used for PCR.

As primers for the PCR, oligonucleotides having the nucleotide sequences shown in SEQ ID NOS: 1 and 2 (their synthesis was consigned to Japan Bioservice Co., Ltd), which has been designed based on the known nucleotide sequences of the purR gene of *Bacillus subtilis* 168 Marburg strain (GenBank accession No. D26185 (the coding region corresponds to the nucleotide numbers 118041–118898), DDJB accession No. Z99104 (the coding region corresponds to the nucleotide numbers 54439–55296). These primers had HindIII and PstI restriction enzyme recognition sequences near the 5' end and 3' end, respectively.

The PCR was performed by repeating a reaction cycle of denaturation at 94° C. for 1 minute, annealing at 45° C. for 1 minute and extension reaction at 72° C. for 1 minute, for 30 cycles in 0.1 ml of PCR reaction solution containing 6 ng/µl of the chromosome DNA and 3 µM of the primers.

The reaction product and plasmid pHSG398 (Takara Shuzo) were digested with HindIII and PstI, and ligated by using a ligation kit (Takara Shuzo). Using the resulting recombinant plasmid, *Escherichia coli* JM109 was transformed. The transformants were cultured on LB agar medium containing 30 µ/ml of chloramphenicol (Cm) and X-Gal (5-bromo-4-chloro-3-indolyl-B-D-galactoside) to obtain white colonies of chloramphenicol resistant transformants. Plasmids were extracted from the transformants obtained as described above, and the plasmid inserted with the target DNA fragment was designated pHSG398BSPR (FIG. 1).

<2> Construction of plasmid containing disrupted purR (ΔpurR)

Plasmid pDG1726 was prepared from *Escherichia coli* ECE101 strain commercially available from Bacillus Genetic Stock Center (BGSC). From the plasmid, spectinomycin resistance (Sp$^r$) gene can be taken out as a cassette.

Figure 2:
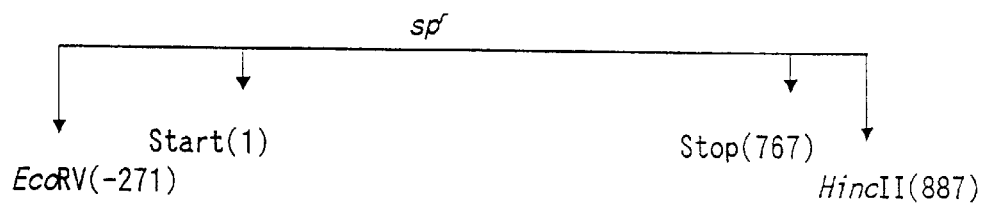
FIG. 2 represents fragments obtained by completely digesting pHSG398BSPR with HincII and EcoRV.
Figure 3:
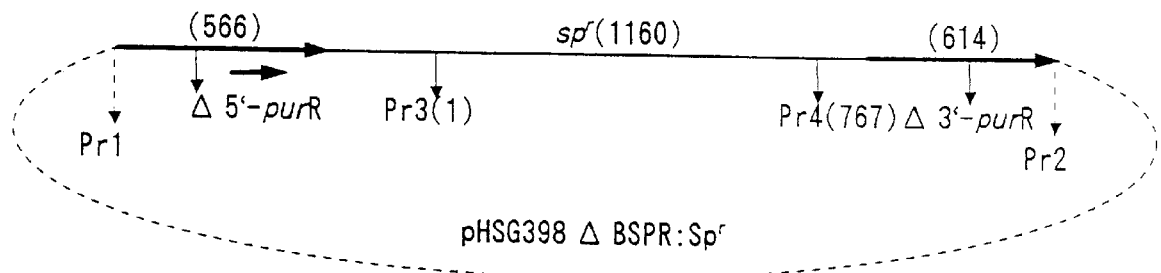
FIG. 3 represents the structure of plasmid pHSG398ΔBSPR:Sp$^r$ for the purR gene disruption. The bold line indicates the disrupted purR gene (ΔpurR) of *Bacillus subtilis* SB112. The parenthesized numbers represent positions in the coding region when the starting position is defined 1. The normal line represents a spectinomycin resistance gene, and the broken line represents plasmid pHSG398.

The plasmids pDG1726 and pHSG398BSPR obtained in <1> were completely (FIG. 2) and partially digested with restriction enzymes HincII and EcoRV, respectively, and treated with phenol. Each DNA was ligated by using the ligation kit, and *Escherichia coli* JM109 was transformed by using the ligation solution, and cultured on LB agar medium containing 50 μg/ml of chloramphenicol and 100 μg/ml of spectinomycin. Plasmid was extracted from the resulting transformant to afford plasmid pHSG398ΔBSPR:Sp$^r$ whose purR gene was disrupted by insertion of the spectinomycin resistance gene (FIG. 3).

<3> Creation of purR gene disrupted strain

Bacillus subtilis SB112 (BGSC 1A227) was transformed with the plasmid pHSG398ΔBSPR:Sp$^r$ obtained in the aforementioned <2>. The transformation was performed by using competent cells prepared according to the method of Ishiwa (Ishiwa H. et al., 1986, Jpn. J. Genet. 61 515–528). The plasmid pHSG398ΔBSPR:Sp$^r$ cannot replicate DNA in Bacillus subtilis cells. However, because the plasmid has regions homologous to the chromosome purR gene at the 5' side and 3' side of the spectinomycin resistance gene, it can undergo gene substitution with the chromosomal purR gene by double crossover recombination.

The aforementioned transformants were cultured on LB agar medium containing 100 μg/ml of spectinomycin, and grown strains were selected to obtain strains in which the chromosomal purR gene was replaced by the ΔBSPR:Sp$^r$ gene. By performing PCR using chromosomal DNA of candidate strain as template, the primers for the purR gene (SEQ ID NO: 1 and 2), and primers for the Sp$^r$ gene having nucleotide sequences shown in SEQ ID NOS: 3 and 4 (their synthesis was consigned to Japan Bioservice Co., Ltd), it was confirmed that the intended gene substitution had occurred based on the size of the ΔBSPR:Sp$^r$ portion and insertion of spectinomycin resistance gene. One of gene substituted strains obtained as described above was designated Bacillus subtilis SB112K.

<4> Production of nucleic acid by purR defective strain

The Bacillus subtilis SB112K strain produced in the aforementioned <3>, and the parent strain, Bacillus subtilis SB112, were cultured overnight in LB and LB agar medium containing 100 μg/ml of spectinomycin at 37° C. overnight, and 3 loops of the cells were inoculated into 20 ml of production medium shown in Table 1, and cultured at 32° C. for 72 hours.

TABLE 1

Composition of fermentation medium

| Medium component | Concentration |
| --- | --- |
| Glucose | 100 g/L |
| NH$_4$Cl | 20 g/L |
| KH$_2$PO$_4$ | 0.5 g/L |
| MgSO$_4$.7H$_2$O | 0.4 g/L |
| FeSO$_4$.7H$_2$O | 2 ppm |
| MnSO$_4$.5H$_2$O | 2 ppm |
| L-Tryptophan | 300 mg/L |
| L-Phenylalanine | 300 mg/L |
| L-glutamic acid | 15.0 g/L |
| DL-methionine | 0.3 g/L |
| Bean concentrate (T-N) | 1.5 g/L |
| Antifoamer (GD-113) | 0.05 ml/L |
| pH modifier (KOH) | 7.2 g/L |

After the cultivation was completed, accumulated amounts of hypoxanthine, uracil, guanosine, guanine, adenosine, and adenine in the culture medium were measured by high performance liquid chromatography. The results are shown in Table 2. In the purR defective strain SB112K, a marked amount of hypoxanthine, i.e., about 600 mg/L, was accumulated, and thus it showed about 20-fold increase of the accumulation compared with the parent strain. As for uracil, the accumulation increased by 5 times compared with the parent strain. Further, accumulation of adenine and guanine, which was not recognized in the parent strain, was also recognized in the purR defective strain.

TABLE 2

Evaluation of fermentation

| Strain | Product (mg/L) | | | |
| --- | --- | --- | --- | --- |
| | Hypoxanthine | uracil | guanine | adenine |
| SB112K | 585 | 166 | 20 | 127 |
| SB112 (parent strain) | 30 | 30 | 0 | 0 |

What is claimed is:

1. A method for producing a nucleic acid substance comprising steps of:
   cultivating in a culture medium a microorganism whose repressor protein for purine operon does not function in a normal manner to produce and accumulate the nucleic acid substance in the culture medium, and
   collecting the substance from the culture medium.

2. The method of claim 1, wherein the repressor protein does not function in a normal manner because a gene encoding the repressor protein on a chromosome of the microorganism is disrupted.

3. The method of claim 1, wherein the repressor protein has the amino acid sequence shown in SEQ ID NO: 6.

4. The method of claim 1, wherein the microorganism is a bacterium belonging to the genus Bacillus.

5. The method of claim 4, wherein the microorganism is *Bacillus subtilis*.

6. The method of claim 1, wherein the nucleic acid substance is a nucleic acid base, nucleoside or nucleotide.

7. The method of claim 6, wherein the nucleic acid substance is selected from the group consisting of hypoxanthine, uracil, guanine and adenine.

* * * * *

SEQUENCE LISTING

<160> NUMBER OF SEQ ID NOS: 6

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: primer for PCR

<400> SEQUENCE: 1
ctcaagcttg aagttgcgat gatcaaaa                                    28

<210> SEQ ID NO 2
<211> LENGTH: 28

-continued

```
<212> TYPE: DNA
<213> ORGANISM: Artificial Sequence
<220> FEATURE:
<223> OTHER INFORMATION: Description of Artificial Sequence: primer for
      PCR

<400> SEQUENCE: 2
ctcctgcaga catattgttg acgataat                                         28

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: primer for
      PCR

<400> SEQUENCE: 3
gtgaggagga tatatttgaa t                                                21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: primer for
      PCR

<400> SEQUENCE: 4
ttataatttt tttaatctgt t                                                21

<210> SEQ ID NO 5
<211> LENGTH: 1200
<212> TYPE: DNA
<213> ORGANISM: Bacillus subtilis
<220> FEATURE:
<221> NAME/KEY: CDS
<222> LOCATION: (259)..(1113)

<400> SEQUENCE: 5
atatgcatcc tgaagttgcg atgatcaaaa accagatgaa acgctttggt gcagatgccg      60
tgttaatgag cgggagcggc ccgacagtgt ttggactggt tcagtatgag tcgaaggtgc     120
agagaattta taacgggtta agaggcttct gcgatcaagt ttatgcggtg agaatgatcg     180
gcgaacagaa cgctcttgat taaatccgta tgttaagtta tattgatctt aaaatattcg     240
gattttgggg gtgagttc atg aag ttt cgt cgc agc ggc aga ttg gtg gac      291
                    Met Lys Phe Arg Arg Ser Gly Arg Leu Val Asp
                      1               5                  10 tta aca aat tat ttg tta acc cat ccg cac gag tta ata ccg cta acc     339
Leu Thr Asn Tyr Leu Leu Thr His Pro His Glu Leu Ile Pro Leu Thr
            15                  20                  25 ttt ttc tct gag cgg tat gaa tct gca aaa tca tcg atc agt gaa gat     387
Phe Phe Ser Glu Arg Tyr Glu Ser Ala Lys Ser Ser Ile Ser Glu Asp
        30                  35                  40 tta aca att att aaa caa acc ttt gaa cag cag ggg att ggt act ttg     435
Leu Thr Ile Ile Lys Gln Thr Phe Glu Gln Gln Gly Ile Gly Thr Leu
    45                  50                  55 ctt act gtt ccc gga gct gcc gga ggc gtt aaa tat att ccg aaa atg     483
Leu Thr Val Pro Gly Ala Ala Gly Gly Val Lys Tyr Ile Pro Lys Met
60                  65                  70                  75 aag cag gct gaa gct gaa gag ttt gtg cag aca ctt gga cag tcg ctg     531
Lys Gln Ala Glu Ala Glu Glu Phe Val Gln Thr Leu Gly Gln Ser Leu
                80                  85                  90
```

```
gca aat cct gag cgt atc ctt ccg ggc ggt tat gta tat tta acg gat      579
Ala Asn Pro Glu Arg Ile Leu Pro Gly Gly Tyr Val Tyr Leu Thr Asp
         95                 100                 105 atc tta gga aag cca tct gta ctc tcc aag gta ggg aag ctg ttt gct      627
Ile Leu Gly Lys Pro Ser Val Leu Ser Lys Val Gly Lys Leu Phe Ala
        110                 115                 120 tcc gtg ttt gca gag cgc gaa att gat gtt gtc atg acc gtt gcc acg      675
Ser Val Phe Ala Glu Arg Glu Ile Asp Val Val Met Thr Val Ala Thr
    125                 130                 135 aaa ggc atc cct ctt gcg tac gca gct gca agc tat ttg aat gtg cct      723
Lys Gly Ile Pro Leu Ala Tyr Ala Ala Ala Ser Tyr Leu Asn Val Pro
140                 145                 150                 155 gtt gtg atc gtt cgt aaa gac aat aag gta aca gag ggc tcc aca gtc      771
Val Val Ile Val Arg Lys Asp Asn Lys Val Thr Glu Gly Ser Thr Val
                160                 165                 170 agc att aat tac gtt tca ggc tcc tca aac cgc att caa aca atg tca      819
Ser Ile Asn Tyr Val Ser Gly Ser Ser Asn Arg Ile Gln Thr Met Ser
            175                 180                 185 ctt gcg aaa aga agc atg aaa acg ggt tca aac gta ctc att att gat      867
Leu Ala Lys Arg Ser Met Lys Thr Gly Ser Asn Val Leu Ile Ile Asp
        190                 195                 200 gac ttt atg aaa gca ggc ggc acc att aat ggt atg att aac ctg ttg      915
Asp Phe Met Lys Ala Gly Gly Thr Ile Asn Gly Met Ile Asn Leu Leu
    205                 210                 215 gat gag ttt aac gca aat gtg gcg gga atc ggc gtc tta gtt gaa gcc      963
Asp Glu Phe Asn Ala Asn Val Ala Gly Ile Gly Val Leu Val Glu Ala
220                 225                 230                 235 gaa gga gta gat gaa cgt ctt gtt gac gaa tat atg tca ctt ctt act     1011
Glu Gly Val Asp Glu Arg Leu Val Asp Glu Tyr Met Ser Leu Leu Thr
                240                 245                 250 ctt tca acc atc aac atg aaa gag aag tcc att gaa att cag aat ggc     1059
Leu Ser Thr Ile Asn Met Lys Glu Lys Ser Ile Glu Ile Gln Asn Gly
            255                 260                 265 aat ttt ctg cgt ttt ttt aaa gac aat ctt tta aag aat gga gag aca     1107
Asn Phe Leu Arg Phe Phe Lys Asp Asn Leu Leu Lys Asn Gly Glu Thr
        270                 275                 280 gaa tca tgacaaaagc agtccacaca aaacatgccc cagcggcaat cgggcctttat    1163
Glu Ser
    285 tcacaaggga ttatcgtcaa caatatgttt tacagct                           1200

<210> SEQ ID NO 6
<211> LENGTH: 285
<212> TYPE: PRT
<213> ORGANISM: Bacillus subtilis

<400> SEQUENCE: 6

Met Lys Phe Arg Arg Ser Gly Arg Leu Val Asp Leu Thr Asn Tyr Leu
 1               5                  10                  15

Leu Thr His Pro His Glu Leu Ile Pro Leu Thr Phe Phe Ser Glu Arg
            20                  25                  30

Tyr Glu Ser Ala Lys Ser Ser Ile Ser Glu Asp Leu Thr Ile Ile Lys
         35                  40                  45

Gln Thr Phe Glu Gln Gln Gly Ile Gly Thr Leu Leu Thr Val Pro Gly
     50                  55                  60

Ala Ala Gly Gly Val Lys Tyr Ile Pro Lys Met Lys Gln Ala Glu Ala
65                  70                  75                  80

Glu Glu Phe Val Gln Thr Leu Gly Gln Ser Leu Ala Asn Pro Glu Arg
                85                  90                  95
```

```
Ile Leu Pro Gly Gly Tyr Val Tyr Leu Thr Asp Ile Leu Gly Lys Pro
            100             105             110

Ser Val Leu Ser Lys Val Gly Lys Leu Phe Ala Ser Val Phe Ala Glu
        115             120             125

Arg Glu Ile Asp Val Val Met Thr Val Ala Thr Lys Gly Ile Pro Leu
    130             135             140

Ala Tyr Ala Ala Ala Ser Tyr Leu Asn Val Pro Val Val Ile Val Arg
145             150             155             160

Lys Asp Asn Lys Val Thr Glu Gly Ser Thr Val Ser Ile Asn Tyr Val
            165             170             175

Ser Gly Ser Ser Asn Arg Ile Gln Thr Met Ser Leu Ala Lys Arg Ser
            180             185             190

Met Lys Thr Gly Ser Asn Val Leu Ile Ile Asp Asp Phe Met Lys Ala
        195             200             205

Gly Gly Thr Ile Asn Gly Met Ile Asn Leu Leu Asp Glu Phe Asn Ala
        210             215             220

Asn Val Ala Gly Ile Gly Val Leu Val Glu Ala Glu Gly Val Asp Glu
225             230             235             240

Arg Leu Val Asp Glu Tyr Met Ser Leu Leu Thr Leu Ser Thr Ile Asn
            245             250             255

Met Lys Glu Lys Ser Ile Glu Ile Gln Asn Gly Asn Phe Leu Arg Phe
            260             265             270

Phe Lys Asp Asn Leu Leu Lys Asn Gly Glu Thr Glu Ser
            275             280             285
```